(12) United States Patent  (10) Patent No.: US 12,082,647 B2
Wang et al.  (45) Date of Patent: Sep. 10, 2024

(54) SEPARATED PROSTHETIC FOOT WITH TRANSVERSE ARCH (71) Applicant: Jilin University, Changchun (CN)

(72) Inventors: Kunyang Wang, Changchun (CN); Lei Ren, Changchun (CN); Zhihui Qian, Changchun (CN); Wei Liang, Changchun (CN); Yifeng Xue, Changchun (CN); Xuewei Lu, Changchun (CN); Haohua Xiu, Changchun (CN); Luquan Ren, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 135 days.

(21) Appl. No.: 17/807,191

(22) Filed: Jun. 16, 2022

(65) Prior Publication Data
US 2022/0400814 A1 Dec. 22, 2022

(30) Foreign Application Priority Data

Jun. 16, 2021 (CN) .......................... 202110667789.6

(51) Int. Cl.
A61F 2/66 (2006.01)
A43B 3/24 (2006.01)
(Continued)

(52) U.S. Cl.
CPC ................ A43B 21/42 (2013.01); A43B 3/24 (2013.01); A43B 13/34 (2013.01); A61F 2/66 (2013.01); A43B 3/246 (2013.01)

(58) Field of Classification Search
CPC ...... A61F 2/66; A61F 2/76; A61F 2002/6614; A61F 2002/6621; A61F 2002/6628;
(Continued)

(56) References Cited

U.S. PATENT DOCUMENTS

2005/0038524 A1* 2/2005 Jonsson .................... A61F 2/66
623/55
2008/0033578 A1* 2/2008 Christensen .............. A61F 2/66
623/53
(Continued)

FOREIGN PATENT DOCUMENTS

CN 1529573 A 9/2004
CN 1988861 A 6/2007
(Continued)

OTHER PUBLICATIONS

Jiang Xiu-Mei; Zhong Bin; Kong Chui-Lin; Qian Zhi-Hui; Zhang Shi-Wu; Zheng Jin-Jin; Design and Gait Simulation of the Bionic Blue Sheep Quadruped Robot; doi: 10.16576/j.cnki. 1007-4414. 2019.03.021; Issue 3, 2019 (vol. 32, Total Issue 161) Mechanical Research and Application; China Academic Journal Electronic Publishing House. http://www.cnki.net.
(Continued)

Primary Examiner — Christie Bahena
(74) Attorney, Agent, or Firm — WC&F IP (57) ABSTRACT A separated prosthetic foot with a transverse arch belongs to the technical field of manufacturing of artificial limbs. The characteristics of the transverse arch of the human foot are combined into the previous transverse-straight carbon fiber foot design to improve the stiffness of the prosthetic foot and reduce the weight of the prosthetic foot. A forefoot part employs a separated curved plate design, and two simple curved plates with different curvatures are used for simulating a complex curved surface of the transverse arch of the human, such that the manufacturing cost is reduced, and the various parts of the sole are non-uniform in stiffness distribution: the outer side of the foot is a single-layer forefoot plate with a smaller curvature and minor stiffness; and the inner side of the foot is a double-layer stacked forefoot plate,
(Continued)

and the lower layer plate has a large radius in curvature and stiffness.

2 Claims, 5 Drawing Sheets

(51) Int. Cl.
*A43B 13/34* (2006.01)
*A43B 21/42* (2006.01)

(58) Field of Classification Search
CPC ...... A61F 2002/6635; A61F 2002/6642; A61F 2002/665; A61F 2002/6657; A61F 2002/6664; A61F 2002/6678
See application file for complete search history.

(56) References Cited

U.S. PATENT DOCUMENTS

| | | | | |
|---|---|---|---|---|
| 2011/0197682 | A1* | 8/2011 | Palmer | G01L 1/2231 |
| | | | | 73/862.045 |
| 2011/0208323 | A1* | 8/2011 | Clausen | A61F 2/66 |
| | | | | 623/55 |
| 2011/0213471 | A1* | 9/2011 | Jonsson | A61F 2/66 |
| | | | | 623/53 |
| 2013/0030549 | A1* | 1/2013 | Zahedi | A61F 2/642 |
| | | | | 623/39 |
| 2013/0110258 | A1* | 5/2013 | Jonsson | A61F 2/66 |
| | | | | 623/55 |
| 2015/0025654 | A1* | 1/2015 | Jonsson | A61F 2/66 |
| | | | | 623/55 |

FOREIGN PATENT DOCUMENTS

| | | | |
|---|---|---|---|
| CN | 101031261 | A | 9/2007 |
| CN | 204521067 | U | 8/2015 |
| CN | 106456341 | A | 2/2017 |
| CN | 206508084 | U | 9/2017 |
| CN | 11821076 | A | 10/2020 |
| CN | 112206084 | A | 1/2021 |
| DE | 102007036021 | A1 | 2/2008 |
| KR | 20170087297 | A * | 7/2017 |

OTHER PUBLICATIONS

Li Fei; Zhang Fu-Ming; Ding Ruo-Xiu; Xie Hua-Long; Mechanism Design and Shock-Absorbing Performance Analysis of Prosthesis Knee Joint with Meniscus; doi: 10.19356/j .; CLC classification No. TH16; Document identification code: A; Article No. 1001-3997 (2016) 01-0161-04; China Academic Journal Electronic Publishing House. http://www.cnki.net.

* cited by examiner

FIG.9

SEPARATED PROSTHETIC FOOT WITH TRANSVERSE ARCH

CROSS REFERENCE TO RELATED APPLICATION

This patent application claims the benefit and priority of Chinese Patent Application No. 202110667789.6, filed on Jun. 16, 2021, the disclosure of which is incorporated by reference herein in its entirety as part of the present application.

TECHNICAL FIELD

The present disclosure belongs to the technical field of the manufacturing of artificial limbs, and in particular relates to a prosthetic foot designed by combining the characteristics of a transverse arch of a human foot and the plantar pressure center change rule.

BACKGROUND ART

Amputation places a burden on individuals, families and societies, while fitting prosthesis to reconstruct a function of independent motion is an effective means to improve the self-care level and the ability of reengaging in social activities of the amputee. As an only part of the human body in contact with the ground for support, the foot is an important part of the lower limb. Prosthetic foot is a prosthetic component for compensating the function of an ankle system of the human body, the performance of which is directly related to the overall function of the prosthesis. The design of prosthetic foot has always been based on the characteristics of the longitudinal arch of human foot as a reference to achieve the purposes of increasing the overall elasticity of the prosthetic foot and reducing the impact during ground-contacting, and the carbon fiber reinforced composites have been widely used in the prosthetic foot with its superior performance. The performance of the carbon fiber composites has a certain directionality, which leads to large strength of the carbon fiber prosthetic foot in a foot length direction, but poor strength in a foot width direction. As the transverse-straight carbon fiber prosthetic foot having a uniform thickness is poor in dynamic response to different road surfaces and different motion states, more ground impact force is transferred to the stump in the ground-contacting bearing period and the supporting and propulsion period of the foot, and therefore, the stability and comfort of the prosthetic foot are limited. Researches in recent years have showed that the characteristics of the transverse arch of the human foot plays an important role in guaranteeing the overall stiffness of the foot, and the non-uniform curvature change of the transverse arch of the human foot plays an important role in guaranteeing the supporting and propulsion effects required by the walking of the human body and adapting to different road surfaces and different motion states. The stiffness of the lateral forefoot of the human foot is significantly smaller than that of the medial forefoot of the human foot, and the plantar pressure center is transferred from the lateral forefoot to the medial forefoot during walking of the human, which just corresponds to the curvature change rule of the transverse arch of the human foot. Therefore, it is necessary to provide a novel prosthetic foot with a transverse arch by further combining the curvature change characteristic of the transverse arch of the human foot on the basis of the characteristics of the longitudinal arch of the human foot, which can improve the overall stiffness of the prosthetic foot and reduce overall weight of the prosthetic foot; the dynamic response and use comfort under different road conditions and different motion states are improved, the machining and manufacturing are easier, the cost of the prosthetic foot is reduced, and thus the life quality and the exercise ability of the disabled can be better improved.

SUMMARY

For the shortcomings of an existing prosthetic foot made of composites, an objective of the present disclosure is to provide a prosthetic foot designed by combining the transverse arch characteristics of a human foot and the plantar pressure center change rule in a gait cycle. The transverse foot arch characteristics of the human foot are combined into the previous transverse straight carbon fiber foot design to improve the stiffness of the prosthetic foot and reduce the weight of the prosthetic foot. A forefoot part employs a separated curved plate design, and two simple curved plates having different curvatures are used for replacing a complex transverse arch curved surface of the human, thus reducing the manufacturing cost. Moreover, the prosthetic foot sole is designed with reference to the plantar pressure center change rule in a gait cycle and an action sequence of various parts of foot on the ground in the gait cycle, such that various parts of the sole are non-uniform in stiffness and can dynamically adapt to stiffness demands on different road surfaces and different walking stages. This will improve the motor performance of the prosthetic foot in terms of shock absorbing, body support and propulsion, stability, and user-comfort.

A separated prosthetic foot with a transverse arch comprises a sole curved plate A, a heel curved plate B, a connecting piece C, a screw and post set I 1, a screw and post set II 2, a rubber gasket 13, a bolt 14, a bolt II 5, and a rubber gasket II 6. The connecting piece C, an upper carbon fiber curved plate 8 of the sole curved plate A, a lower carbon fiber curved plate 7 of the sole curved plate A, and the rubber gasket II 6 are sequentially arranged from bottom to top; the heel curved plate B, the lower carbon fiber curved plate 7 and the upper carbon fiber curved plate 8 of the sole curved plate A and the connecting piece are sequentially arranged from bottom to top, wherein the rubber gasket II 6 is located below the rear part of the lower carbon fiber curved plate 7; the rubber gasket II 6, the rear parts of the lower carbon fiber curved plate 7 and the upper carbon fiber curved plate 8 of the sole curved plate A and the bottom surface of a main body 10b of the connecting piece C are fixedly connected by the bolt I 4 and the bolt II 5; the rubber gasket 13 is located below the front part of the heel curved plate B; the rubber gasket 13, the front part of the heel curved plate B, and the middle parts of the lower carbon fiber curved plate 7 and the upper carbon fiber curved plate 8 of the sole curved plate A are fixedly connected by the screw and post set I1 and the screw and post set II 2; the bottom surface of the main body 10b in the connecting piece C is the same as the arc curved surface of the rear arc part III 8a of the upper carbon fiber curved plate 8 in the sole curved plate A in size.

The sole curved plate A consists of the upper carbon fiber curved plate 8 and the lower carbon fiber curved plate 7; the upper carbon fiber curved plate 8 consists of a rear arc part III 8a, a rear arc part IV 8b, a middle transition part III 8c, a middle transition part IV 8d and a front flat-folded plate part 8e; the rear arc part III 8a, the rear arc part IV 8b, middle transition part III 8c, the middle transition part IV 8d and the front flat-folded plate part 8e are smoothly connected into a whole in sequence from back to front; the rear arc part III 8a is provided with a rear hole III 8i and a rear hole IV 8h, the rear arc part IV 8b is provided with a front hole III 8g and a front hole IV 8f, the rear arc part III 8a and the rear arc part IV 8b are both arc curved surfaces having a uniform curvature, an arc radius of 65 to 70 mm, and a central angle of 70 to 80 degrees; the front flat-folded plate part 8e is controlled by a fold line which is formed by connecting two straight lines having a height difference of 2 mm through arc smooth transition; the shapes of the middle transition part III 8c and the middle transition part IV 8d change from arc transition to straight, and the curvature changes from large to small; the lower carbon fiber curved plate 7 consists of a rear arc part I 7a, a rear arc part II 7b, a middle transition part I 7c, a middle transition part II 7d and a front flat plate part 7e; the rear arc part I 7a, the rear arc part II 7b, the middle transition part I 7c, the middle transition part II 7d and the front flat plate part 7e are smoothly connected into a whole in sequence from back to front; the rear arc part I 7a is provided with a rear hole I 7i and a rear hole II 7h, and the rear arc part II 7b is provided with a front hole I 7g and a front hole II 7f, wherein the rear arc part I 7a and the rear arc part II 7b are arc curved surfaces having a uniform curvature which is greater than the curvature of the rear arc part III 8a and the rear arc part IV 8b, a circular arc radius of 35 to 40 mm, and a central angle of 55 to 65 degrees; the front flat plate part 7e is a flat plate, and the area of the front flat plate part is smaller than that of the front flat-folded plate part 8e; the shapes of the middle transition part I 7c and the middle transition part II 7d change from arc transition to straight, and the curvature changes from large to small; the upper carbon fiber curved plate 8 is located one the lower carbon fiber curved plate 7, the bottom surface of the upper carbon fiber curved plate 8 is in close contact with the top surface of the lower carbon fiber curved plate 7, and the front flat plate part 7e of the lower carbon fiber curved plate 7 is embedded in the front flat-folded plate part 8e of the upper carbon fiber curved plate 8; the rear hole I 7i, the rear hole II 7h, the front hole I 7g and the front hole II 7f respectively correspond to the rear hole III 8i, the rear hole IV 8h, the front hole III 8g and the front hole IV 8f up and down in sequence; the upper carbon fiber curved plate 8 and the lower carbon fiber curved plate 7 are integrally controlled by a sole longitudinal curve D in a front-back direction, the sole longitudinal curve D consists of a sole longitudinal curve section I 7j and a sole longitudinal curve section II 7k, and the sole longitudinal curve section I 7j is a straight line section with an inclination angle α7j ranging from 18 degrees to 20 degrees; the sole longitudinal curve section II 7k is a section of downward convex arc having an arc radius of 230 to 240 mm and a central angle of 20 to 22 degrees; the sole longitudinal curve section II 7k is located at the front part of the sole longitudinal curve D, and the sole longitudinal curve section I 7j and the sole longitudinal curve section II 7k are in smooth and tangent connection.

The heel curved plate B consists of a top arc part 9a, a middle buffering transition part I 9b, a middle buffering transition part II 9c and a bottom flat plate part 9d; the top arc part 9a, the middle buffering transition part I 9b, the middle buffering transition part II 9c and the bottom flat plate part 9d are smoothly connected into a whole in sequence from front to back; the top arc part 9a is a curved surface having a straight line in a front-back direction and an arc in a left-right direction, and having an arc radius of 30 to 35 mm and an central angle of 40 to 50 degrees, and the top arc part 9a is provided with a through hole I 9e and a through hole II 9f; the bottom flat plate part 9d is a straight plate having a width greater than that of the top arc part 9a; the shapes of the middle buffering transition part I 9b and the middle buffering transition part II 9c change from arc smooth transition to straight, the curvature changes from large to small, the width changes from small to large, such that the heel curved plate is fan-shaped; during the transition from the top arc part 9a to the bottom flat plate part 9d, the thickness of the heel curved plate changes from 4 mm to 2.5 mm; the heel curved plate B is integrally controlled by a heel longitudinal curve E in a front-back direction, and the heel longitudinal curve E consists of a heel longitudinal curve section I 9g, a heel longitudinal curve section II 9h and a heel longitudinal curve section III 9i; the heel longitudinal curve I section 9g is a downward convex arc having an arc radius of 70 to 75 mm and a central angle of 38 to 42 degrees; the heel longitudinal curve II section 9h is an upward convex arc having an arc radius of 35 to 40 mm and a central angle of 55 to 60 degrees; the heel longitudinal curve section III 9i is a straight line with an inclination angle α9i of 18 to 20 degrees; the heel longitudinal curve I section 9g, the heel longitudinal curve II section 9h and the heel longitudinal curve III section 9i are in smooth and tangent connection in sequence from back to front.

The connecting piece C consists of a square conical head 10a and the main body 10b, wherein the middle of the main body 10b is provided with a cavity 10e, the bottom end of the main body 10b is provided with a threaded hole I 10c and a threaded hole II 10d; the square conical head 10a is fixedly connected to the center of the upper end of the main body 10b, the bottom surface of the main body 10b is an arc curved surface having an arc radius of 65 to 70 mm and a central angle of 65 to 75 degrees.

Corresponding to a gait cycle of a normal person, the plantar pressure center gradually moves forwards from the heel to the lateral forefoot and then is gradually transferred from the lateral forefoot to the medial forefoot, the plantar pressure borne by human foot in different ground-contacting stages is different, and the stiffness required by different parts of the human foot is also different. In a ground-contacting process of the prosthetic foot in one gait cycle, the gravity center of the body is located on the heel curved plate B and then is gradually transferred from the heel curved plate B to the outer side of the sole curved plate A, i.e., the outer side of the front flat-folded plate part 8e of the upper carbon fiber curved plate 8 in the sole curved plate A, at the moment, only the front flat-folded plate part 8e of the upper carbon fiber bent plate 8 is stressed, and due to small curvature, small stiffness and large deformation amount after being stressed, the front flat-folded plate part 8e of the upper carbon fiber bent plate 8 can better adapt to various road conditions, and can absorb the impact of the foot in the landing process in the normal motion process to play a role in buffering and energy storage, and can also adapt to bumpy road surfaces, thus making the prosthetic foot have better stability and comfort in the process of walking on different road surfaces. Afterwards, the gravity center of the body is transferred from the outer side of the sole curved plate A to the inner side, i.e., the front flat plate part 7e of the lower carbon fiber curved plate 7 and the inner side of the front flat-folded plate part 8e of the upper carbon fiber curved plate 8 in the sole curved plate A, and at the moment, the lower carbon fiber curved plate 7 and the upper carbon fiber curved plate 8 in the sole curved plate A are stacked together to be stressed jointly, the thickness of the equivalent carbon fiber plate formed integrally is large; and as the curvature of the lower carbon fiber curved plate 7 is larger than that of the upper carbon fiber curved plate 8, the equivalent stiffness is larger after the two curved plates are stacked, and the supporting and propulsion effects in the gait cycle are better.

The present disclosure has the beneficial effects that:

1. The transverse arch of a human foot plays an important role in guaranteeing the stiffness of the human foot. In accordance with the present disclosure, the characteristics of the transverse arch of the human body are combined into the prosthetic foot containing only the characteristics of a longitudinal arch, the transverse-straight carbon fiber plate is changed into the transverse-bent carbon fiber plate, such that the weight of the prosthetic foot is greatly reduced while the stiffness required by the use of the prosthetic foot is ensured. Meanwhile, the sole part employs a separated curved plate design, and two simple curved plates having different curvatures are used for replacing a complex transverse arch curved surface of the human body, thus reducing the manufacturing cost.

2. A double-layer separated prosthetic foot sole is designed with reference to the characteristics of a plantar pressure center line in the gait cycle and the action sequence of various parts of the foot on the ground in the gait cycle, such that the various parts of the sole are non-uniform in stiffness distribution. The outer side of the prosthetic foot is a single-layer forefoot plate with a smaller curvature and small stiffness; the inner side of the prosthetic foot is a double-layer forefoot plate with a large curvature and large stiffness; and different curvatures and different thicknesses can dynamically meet the stiffness requirements of different road surfaces and different walking stages, further improving the motor performance in terms of shock absorbing, body support and propulsion, stability, and user-comfort.

BRIEF DESCRIPTION OF THE DRAWINGS

In the drawings: A—sole curved plate; B—heel curved plate; C—connecting piece; D—sole longitudinal curve; E—heel longitudinal curve; 1—screw and post set I; 2—screw and post set II; 3—rubber gasket I; 4—bolt I; 5—bolt II; 6—rubber gasket II; 7—lower carbon fiber curved plate; 7*a*—rear arc part I; 7*b*—rear arc part II; 7*c*—middle transition part I; 7*d*—middle transition part II; 7*e*—front flat plate part; 7*f*—front hole II; 7*g*—front hole I; 7*h*—rear hole II; 7*i*—rear hole I; 7*j*—sole longitudinal curve section I; 7*k*—sole longitudinal curve section II; 8—upper carbon fiber curved plate; 8*a*—rear arc part III; 8*b*—rear arc part IV; 8*c*—middle transition part III; 8*d*—middle transition part IV; 8*e*—front flat-folded plate part; 8*f*—front hole IV; 8*g*—front hole III; 8*h*—rear hole IV; 8*i*—rear hole III; 9*a*—top arc part; 9*b*—middle buffering transition part I; 9*c*—middle buffering transition part II; 9*d*—bottom flat plate part; 9*e*—through hole I; 9*f*—through hole II; 9*g*—heel longitudinal curve section I; 9*h*—heel longitudinal curve section II; 9*i*—heel longitudinal curve section III; 10*a*—square conical head; 10*b*—main body; 10*c*—threaded hole I; 10*d*—threaded hole II; 10*e*—cavity; R7*a*—arc radius of rear arc part I; R7*b*—arc radius of rear arc part II; R7*k*—arc radius of sole longitudinal curve section II; R8*a*—arc radius of rear arc part III; R8*b*—arc radius of rear arc part IV; R9*a*—arc radius of top arc part; R9*g*—arc radius of heel longitudinal curve section I; R9*h*—arc radius of heel longitudinal curve section I; R10*b*—arc radius of threaded hole II; θ7*a*—central angle of rear arc part I; θ7*b*—central angle of rear arc part II; θ7*k*—central angle of sole longitudinal curve section II; θ8*a*—central angle of rear arc part III; θ8*b*—central angle of rear arc part IV; θ9*a*—central angle of top arc part; θ9*g*—central angle of heel longitudinal curve section I; θ9*h*—central angle of heel longitudinal curve section I; θ10*b*—central angle of threaded hole II; T—thickness of the curved heel plate, α7*j*—inclination angle of the sole longitudinal curve section I relative to the horizontal plane; and α9*i*—inclination angle of the heel longitudinal curve section III relative to the horizontal plane.

DETAILED DESCRIPTION OF THE EMBODIMENTS

The following describes the present disclosure with reference to the accompanying drawings.

As shown in FIG. 1 to FIG. 4, a separated prosthetic foot with a transverse arch comprises a sole curved plate A, a heel curved plate B, a connecting piece C, a screw and post set I 1, a screw and post set II 2, a rubber gasket I3, a bolt I 4, a bolt II 5, and a rubber gasket II 6. The connecting piece C, an upper carbon fiber curved plate 8 of the sole curved plate A, a lower carbon fiber curved plate 7 of the sole curved plate A, and the rubber gasket II 6 are sequentially arranged from bottom to top; the heel curved plate B, the lower carbon fiber curved plate 7 and the upper carbon fiber curved plate 8 of the sole curved plate A and the connecting piece are sequentially arranged from bottom to top, wherein the rubber gasket II 6 is located below the rear part of the lower carbon fiber curved plate 7; the rubber gasket II 6, the rear parts of the lower carbon fiber curved plate 7 and the upper carbon fiber curved plate 8 of the sole curved plate A and the bottom surface of a main body 10*b* of the connecting piece C are fixedly connected by the bolt I 4 and the bolt II 5; the rubber gasket 13 is located below the front part of the heel curved plate B; the rubber gasket 13, the front part of the heel curved plate B, and the middle parts of the lower carbon fiber curved plate 7 and the upper carbon fiber curved plate 8 of the sole curved plate A are fixedly connected by the screw and post set I1 and the screw and post set II 2; the bottom surface of the main body 10*b* in the connecting piece C is the same as the arc curved surface of the rear arc part III 8*a* of the upper carbon fiber curved plate 8 in the sole curved plate A in size.

Figure 1:
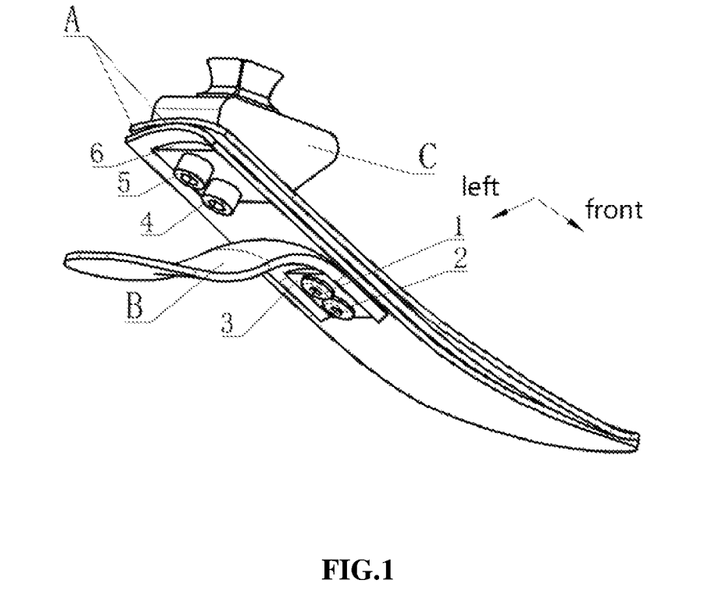
FIG. 1 is an axonometric view (rear right direction) of a separated prosthetic foot with a transverse arch.
Figure 2:
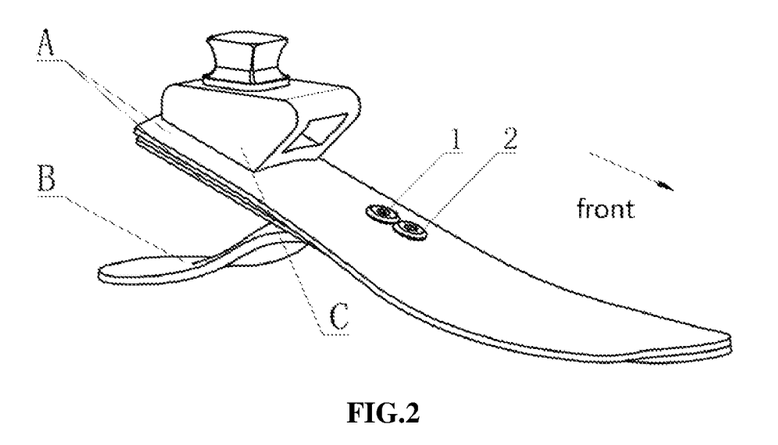
FIG. 2 is an axonometric view (front right direction) of a separated prosthetic foot with a transverse arch.
Figure 3:
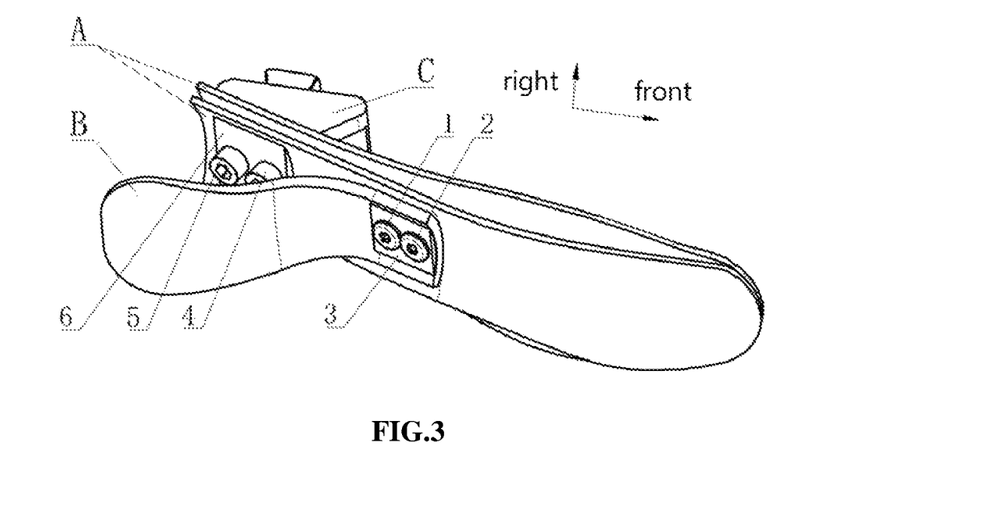
FIG. 3 is an axonometric view (right bottom direction) of a separated prosthetic foot with a transverse arch.
Figure 4:
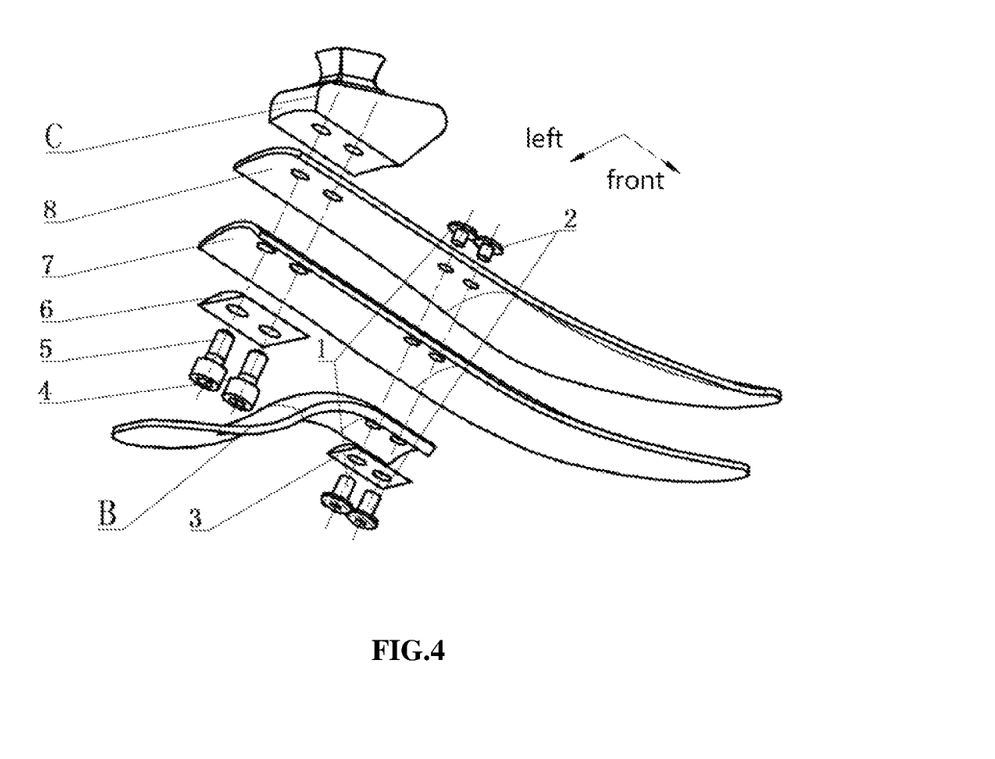
FIG. 4 is an exploded view (front right direction) of a separated prosthetic foot with a transverse arch.
Figure 5:
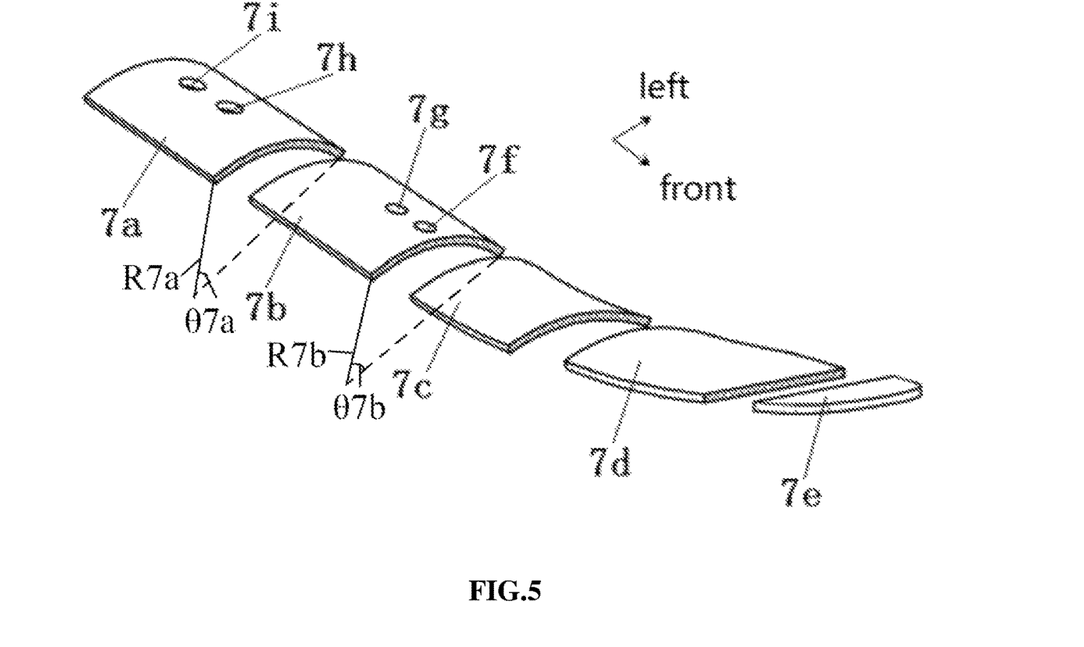
FIG. 5 is an axonometric view (front right direction) of a segmented section of an upper carbon fiber curved plate 8.
Figure 6:
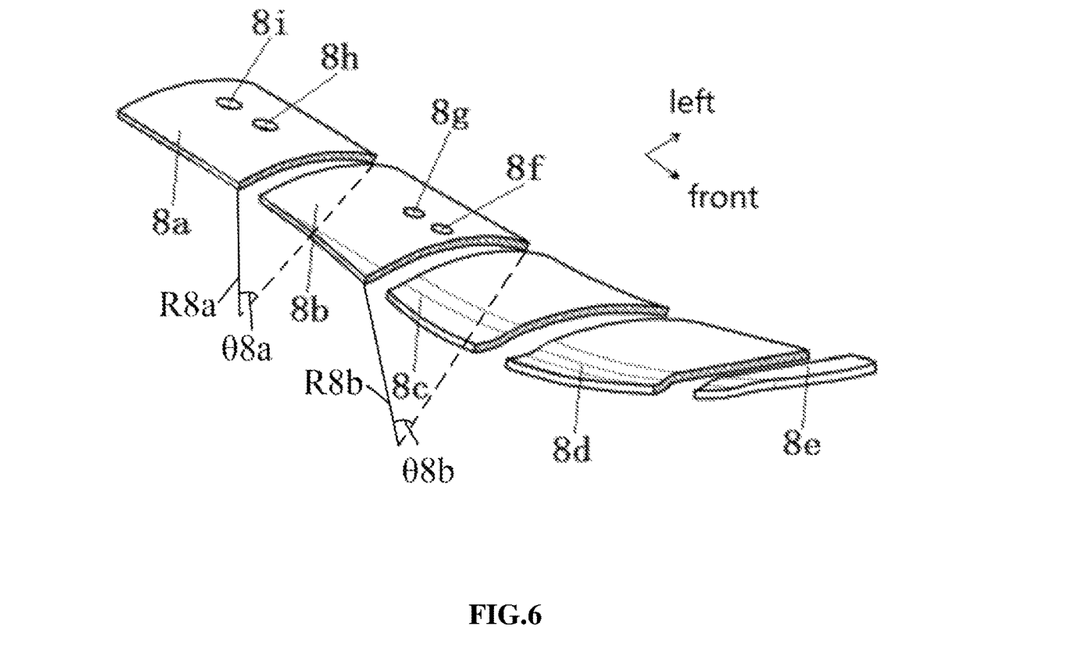
FIG. 6 is an axonometric view (front right direction) of a segmented section of a lower carbon fiber curved plate 7.
Figure 8:
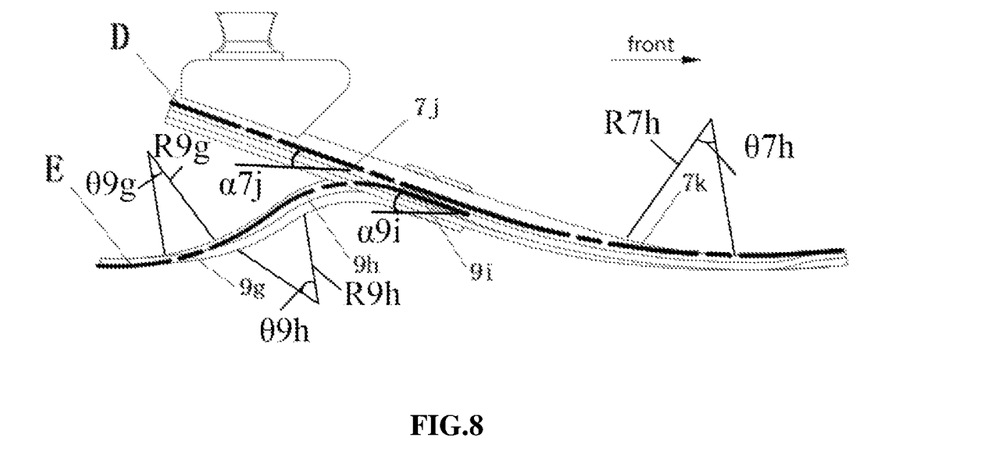
FIG. 8 is a right view of a sole longitudinal curve D and a heel longitudinal curve E.

As shown in FIG. 5, FIG. 6 and FIG. 8, the sole curved plate A consists of the upper carbon fiber curved plate 8 and the lower carbon fiber curved plate 7; the upper carbon fiber curved plate 8 consists of a rear arc part III 8*a*, a rear arc part IV 8*b*, a middle transition part III 8*c*, a middle transition part IV 8*d* and a front flat-folded plate part 8*e*; the rear arc part III 8*a*, the rear arc part IV 8*b*, the middle transition part III 8*c*, the middle transition part IV 8*d* and the front flat-folded plate part 8*e* are smoothly connected into a whole in sequence from back to front; the rear arc part III 8*a* is provided with a rear hole III 8i and a rear hole IV 8h, the rear arc part IV 8b is provided with a front hole III 8g and a front hole IV 8f; the rear arc part III 8a and the rear arc part IV 8b are both arc curved surfaces having a uniform curvature, an arc radius (R8a, R8b) of 65 to 70 mm, and a central angle (θ8a, θ8b) of 70 to 80 degrees; the front flat-folded plate part 8e is controlled by a fold line which is formed by connecting two straight lines having a height difference of 2 mm through arc smooth transition; the shapes of the middle transition part III 8c and the middle transition part IV 8d change from arc transition to straight, and the curvature changes from large to small; the lower carbon fiber curved plate 7 consists of a rear arc part I 7a, a rear arc part II 7b, a middle transition part I 7c, a middle transition part II 7d and a front flat plate part 7e; the rear arc part I 7a, the rear arc part II 7b, the middle transition part I 7c, the middle transition part II 7d and the front flat plate part 7e are smoothly connected into a whole in sequence from back to front; the rear arc part I 7a is provided with a rear hole I 7i and a rear hole II 7h, and the rear arc part II 7b is provided with a front hole I 7g and a front hole II 7f, wherein the rear arc part I 7a and the rear arc part II 7b are arc curved surfaces having a uniform curvature which is greater than the curvature of the rear arc part III 8a and the rear arc part IV 8b, a circular arc radius (R7a, R7b) of 35 to 40 mm, and a central angle (θ7a, θ7b) of 55 to 65 degrees; the front flat plate part 7e is a flat plate, and the area of the front flat plate part is smaller than that of the front flat-folded plate part 8e; the shapes of the middle transition part I 7c and the middle transition part II 7d change from arc transition to straight, and the curvature changes from large to small; the upper carbon fiber curved plate 8 is located one the lower carbon fiber curved plate 7, the bottom surface of the upper carbon fiber curved plate 8 is in close contact with the top surface of the lower carbon fiber curved plate 7, and the front flat plate part 7e of the lower carbon fiber curved plate 7 is embedded in the front flat-folded plate part 8e of the upper carbon fiber curved plate 8; the rear hole I 7i, the rear hole II 7h, the front hole I 7g and the front hole II 7f respectively correspond to the rear hole III 8i, the rear hole IV 8h, the front hole III 8g and the front hole IV 8f up and down in sequence; the upper carbon fiber curved plate 8 and the lower carbon fiber curved plate 7 are integrally controlled by a sole longitudinal curve D in a front-back direction, the sole longitudinal curve D consists of a sole longitudinal curve section I 7j and a sole longitudinal curve section II 7k, and the sole longitudinal curve section I 7j is a straight line section with an inclination angle α7j ranging from 18 degrees to 20 degrees; the sole longitudinal curve section II 7k is a section of downward convex arc having an arc radius R7k of 230 to 240 mm and a central angle θ7k of 20 to 22 degrees; the sole longitudinal curve section II 7k is located at the front part of the sole longitudinal curve D, and the sole longitudinal curve section I 7j and the sole longitudinal curve section II 7k are in smooth and tangent connection.

Figure 7:
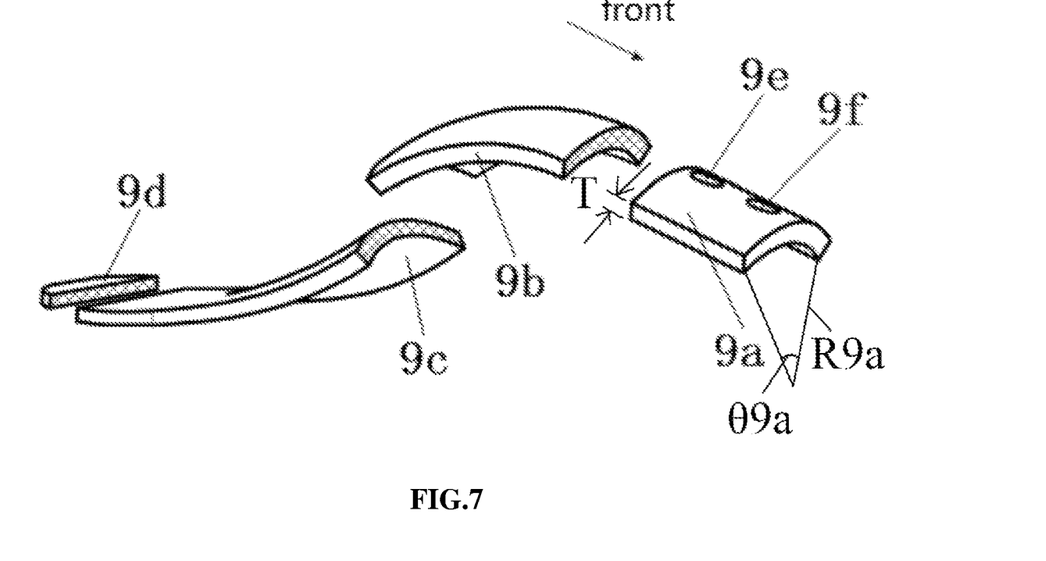
FIG. 7 is an axonometric view (front right direction) of a segmented section of a heel curved plate B.

As shown in FIG. 7 and FIG. 8, the heel curved plate B consists of a top arc part 9a, a middle buffering transition part I 9b, a middle buffering transition part II 9c and a bottom flat plate part 9d; the top arc part 9a, the middle buffering transition part I 9b, the middle buffering transition part II 9c and the bottom flat plate part 9d are smoothly connected into a whole in sequence from front to back; the top arc part 9a is a curved surface having a straight line in a front-back direction and an arc in a left-right direction, and having an arc radius R9a of 30 to 35 mm and an central angle θ9a of 40 to 50 degrees, and the top arc part 9a is provided with a through hole I 9e and a through hole II 9f, the bottom flat plate part 9d is a straight plate having a width greater than that of the top arc part 9a; the shapes of the middle buffering transition part I 9b and the middle buffering transition part II 9c change from arc smooth transition to straight, the curvature changes from large to small, the width changes from small to large, such that the heel curved plate is fan-shaped; during the transition from the top arc part 9a to the bottom flat plate part 9d, the thickness of the heel curved plate changes from 4 mm to 2.5 mm; the heel curved plate B is integrally controlled by a heel longitudinal curve E in a front-back direction, and the heel longitudinal curve E consists of a heel longitudinal curve section I 9g, a heel longitudinal curve section II 9h and a heel longitudinal curve section III 9i; the heel longitudinal curve I section 9g is a downward convex arc having an arc radius R9g of 70 to 75 mm and a central angle θ9g of 38 to 42 degrees; the heel longitudinal curve II section 9h is an upward convex arc having an arc radius R9h of 35 to 40 mm and a central angle θ9h of 55 to 60 degrees; the heel longitudinal curve section III 9i is a straight line with an inclination angle α9i of 18 to 20 degrees; the heel longitudinal curve I section 9g, the heel longitudinal curve II section 9h and the heel longitudinal curve III section 9i are in smooth and tangent connection in sequence from back to front.

Figure 9:
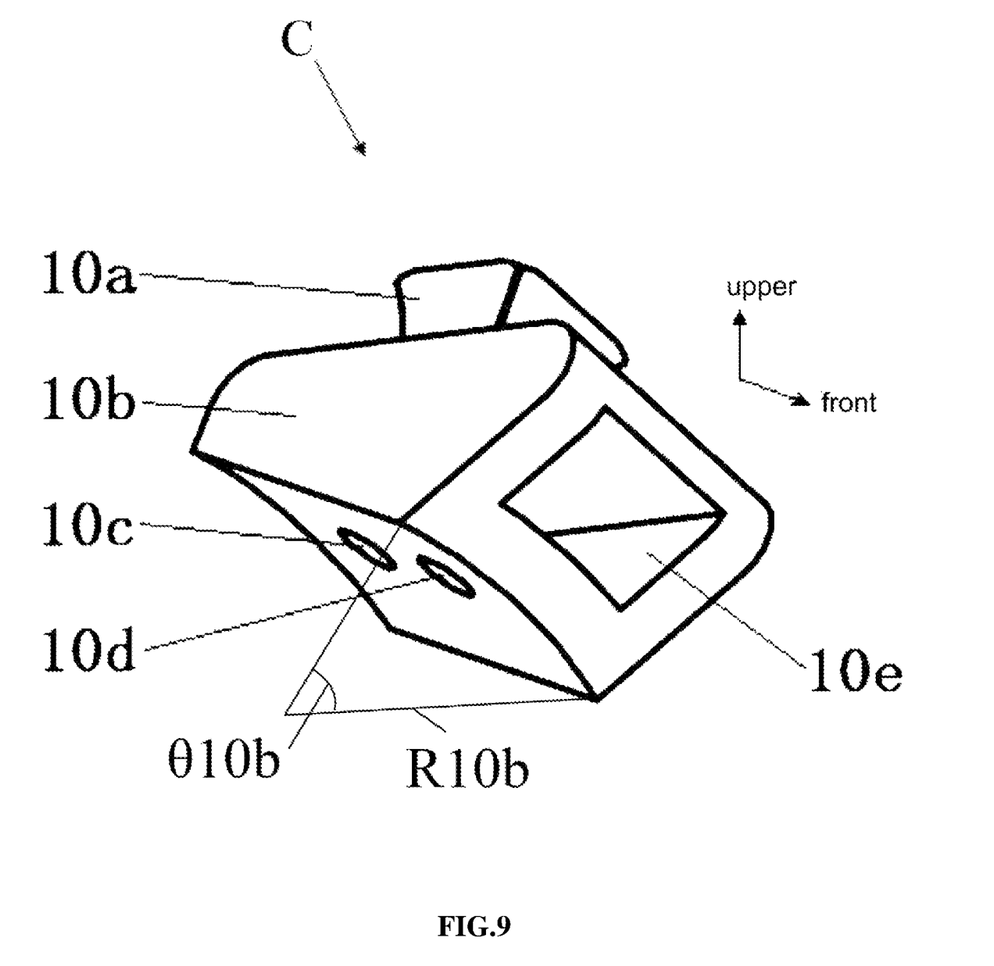
FIG. 9 is an axonometric view (front right direction) of a connecting piece.

As shown in FIG. 9, the connecting piece C consists of a square conical head 10a and the main body 10b, wherein the middle of the main body 10b is provided with a cavity 10e, the bottom end of the main body 10b is provided with a threaded hole I 10c and a threaded hole II 10d; the square conical head 10a is fixedly connected to the center of the upper end of the main body 10b, the bottom surface of the main body 10b is an arc curved surface having an arc radius R10b of 65 to 70 mm and a central angle θ10b of 65 to 75 degrees.

What is claimed is:

1. A separated prosthetic foot with a transverse arch, consisting of a curved sole plate, a curved heel plate, a connecting piece consisting of a square conical head and a main body, a screw and post set I, a screw and post set II, a rubber gasket I, a bolt I, a bolt II and a rubber gasket II, wherein the curved sole plate consists of an upper carbon fiber curved plate and a lower carbon fiber curved plate; the upper carbon fiber curved plate consists of a rear arc part III, a rear arc part IV, a middle transition part III, a middle transition part IV and a front flat polygonal plate part; the rear arc part III, the rear arc part IV, the middle transition part III, the middle transition part IV and the front flat polygonal plate part are smoothly connected into a whole in sequence from back to front; the rear arc part III is provided with a rear hole III and a rear hole IV, the rear arc part IV is provided with a front hole III and a front hole IV; the rear arc part III and the rear arc part IV are both arc curved surfaces having a uniform curvature, an arc radius of 65 to 70 mm, and a central angle of 70 to 80 degrees; profile of the front flat polygonal plate part is defined by a polygonal line which is formed by connecting two straight lines having a height difference of 2 mm through arc smooth transition; the shapes of the middle transition part III and the middle transition part IV transition from an arc to a straight shape, and the curvature decreases; the lower carbon fiber curved plate consists of a rear arc part I, a rear arc part II, a middle transition part I, a middle transition part II and a front flat plate part; the rear arc part I, the rear arc part II, the middle transition part I, the middle transition part II and the front flat plate part are smoothly connected into a whole in sequence from back to front; the rear arc part I is provided with a rear hole I and a rear hole II, and the rear arc part II is provided with a front hole I and a front hole II, wherein the rear arc part I and the rear arc part II are arc curved surfaces having a uniform curvature which is greater than the curvature of the rear arc part III and the rear arc part IV, a circular arc radius of 35 to 40 mm, and a central angle of 55 to 65 degrees; the front flat plate part is a flat plate, and the area of the front flat plate part is smaller than that of the front flat polygonal plate part; the shapes of the middle transition part I and the middle transition part II transition from an arc to a straight shape, and the curvature decreases; the upper carbon fiber curved plate is located on the lower carbon fiber curved plate, the bottom surface of the upper carbon fiber curved plate is in contact with the top surface of the lower carbon fiber curved plate, and the front flat plate part of the lower carbon fiber curved plate is embedded in the front flat polygonal plate part of the upper carbon fiber curved plate; the rear hole I, the rear hole II, the front hole I and the front hole II respectively correspond to the rear hole III, the rear hole IV, the front hole III and the front hole IV vertically in sequence; curvatures of the upper carbon fiber curved plate and the lower carbon fiber curved plate in a front-back direction are generally defined by a sole longitudinal curve, the sole longitudinal curve consists of a sole longitudinal curve section I and a sole longitudinal curve section II, and the sole longitudinal curve section I is a straight line section with an inclination angle ranging from 18 degrees to 20 degrees; the sole longitudinal curve section II is a section of downward convex arc having an arc radius of 230 to 240 mm and a central angle of 20 to 22 degrees; the sole longitudinal curve section II is located at the front part of the sole longitudinal curve, and the sole longitudinal curve section I and the sole longitudinal curve section II are in smooth and tangent connection; the curved heel plate consists of a top arc part, a middle buffering transition part I, a middle buffering transition part II and a bottom flat plate part; the top arc part, the middle buffering transition part I, the middle buffering transition part II and the bottom flat plate part are smoothly connected into a whole in sequence from front to back; the top arc part is a curved surface having a straight line in a front-back direction and an arc in a left-right direction, and having an arc radius of 30 to 35 mm and a central angle of 40 to 50 degrees, and the top arc part is provided with a through hole I and a through hole II; the bottom flat plate part is a straight plate having a width greater than that of the top arc part; the shapes of the middle buffering transition part I and the middle buffering transition part II transitions from an arc to a straight shape, the curvature decreases, the width increases, such that the curved heel plate is fan-shaped; during the transition from the top arc part to the bottom flat plate part, the thickness of the curved heel plate changes from 4 mm to 2.5 mm; curvature of the curved heel plate in a front-back direction is generally defined by a heel longitudinal curve, and the heel longitudinal curve consists of a heel longitudinal curve section I, a heel longitudinal curve section II and a heel longitudinal curve section III; the heel longitudinal curve I section is a downward convex arc having an arc radius of 70 to 75 mm and a central angle of 38 to 42 degrees; the heel longitudinal curve II section is an upward convex arc having an arc radius of 35 to 40 mm and a central angle of 55 to 60 degrees; the heel longitudinal curve section III is a straight line with an inclination angle of 18 to 20 degrees; the heel longitudinal curve I section, the heel longitudinal curve II section and the heel longitudinal curve III section are in smooth and tangent connection in sequence from back to front; the connecting piece (C), the upper carbon fiber curved plate of the curved sole plate, the lower carbon fiber curved plate of the curved sole plate and the rubber gasket II are sequentially arranged from bottom to top; the curved heel plate, the lower carbon fiber curved plate and the upper carbon fiber curved plate of the curved sole plate and the connecting piece (C) are sequentially arranged from bottom to top; wherein the rubber gasket II is positioned below the rear part of the lower carbon fiber curved plate, and the rubber gasket II, the rear parts of the lower carbon fiber curved plate and the upper carbon fiber curved plate in the curved sole plate and the bottom surface of the main body are fixedly connected by a bolt I and a bolt II; the rubber gasket I is positioned below the front part of the curved heel plate; the rubber gasket I, the front part of the curved heel plate, and the middle parts of the lower carbon fiber curved plate and the upper carbon fiber curved plate in the curved sole plate are fixedly connected by the screw and post set I and the screw and post set II; the bottom surface of the main body is the same as the arc curved surface of the rear arc part III of the upper carbon fiber curved plate in the curved sole plate in size.

2. The separated prosthetic foot with the transverse arch according to claim 1, wherein the middle of the main body is provided with a cavity, the bottom end of the main body is provided with a threaded hole I and a threaded hole II; the square conical head is fixedly connected to the center of the upper end of the main body, the bottom surface of the main body is an arc curved surface having an arc radius of 65 to 70 mm and a central angle of 65 to 75 degrees.

\* \* \* \* \*